(12) United States Patent
Wang et al.

(10) Patent No.: US 10,695,693 B2
(45) Date of Patent: Jun. 30, 2020

(54) USE OF ALKALINE WASHES DURING CHROMATOGRAPHY TO REMOVE IMPURITIES

(71) Applicant: BRISTOL-MYERS SQUIBB COMPANY, Princeton, NJ (US)

(72) Inventors: Jue Wang, Bridgewater, NJ (US); Neil E. Jaffe, Newtown, PA (US); Krina Patel, Easton, PA (US)

(73) Assignee: BRISTOL-MYERS SQUIBB COMPANY, Princeton, NJ (US)

( * ) Notice: Subject to any disclaimer, the term of this patent is extended or adjusted under 35 U.S.C. 154(b) by 234 days.

(21) Appl. No.: 15/558,033

(22) PCT Filed: Mar. 11, 2016

(86) PCT No.: PCT/US2016/021984
§ 371 (c)(1),
(2) Date: Sep. 13, 2017

(87) PCT Pub. No.: WO2016/149088
PCT Pub. Date: Sep. 22, 2016

(65) Prior Publication Data
US 2018/0078876 A1 Mar. 22, 2018

Related U.S. Application Data

(60) Provisional application No. 62/132,974, filed on Mar. 13, 2015.

(51) Int. Cl.
| | | |
|---|---|---|
| B01D 15/38 | (2006.01) | |
| C07K 1/22 | (2006.01) | |
| C07K 16/00 | (2006.01) | |
| B01D 15/20 | (2006.01) | |
| B01D 15/42 | (2006.01) | |
| G01N 30/50 | (2006.01) | |
| C07K 16/06 | (2006.01) | |
| B01D 15/18 | (2006.01) | |
| G01N 30/88 | (2006.01) | |

(52) U.S. Cl.
CPC ......... B01D 15/20 (2013.01); B01D 15/1871 (2013.01); B01D 15/3809 (2013.01); B01D 15/424 (2013.01); C07K 1/22 (2013.01); C07K 16/00 (2013.01); C07K 16/065 (2013.01); G01N 30/50 (2013.01); C07K 2317/21 (2013.01); G01N 2030/8831 (2013.01)

(58) Field of Classification Search
None
See application file for complete search history.

(56) References Cited

U.S. PATENT DOCUMENTS

| | | | | |
|---|---|---|---|---|
| 5,190,859 A | * | 3/1993 | Dustin | ............ C07K 14/70528 435/2 |
| 6,172,197 B1 | | 1/2001 | McCafferty et al. | |
| 6,339,142 B1 | * | 1/2002 | Basey | ....................... C07K 1/18 530/387.3 |
| 6,870,034 B2 | | 3/2005 | Breece et al. | |
| 7,763,706 B1 | | 7/2010 | Dekker et al. | |
| 8,058,410 B2 | * | 11/2011 | Jungbauer | ................ C07K 1/22 530/413 |
| 8,350,013 B2 | | 1/2013 | Sun | |
| 2009/0306351 A1 | * | 12/2009 | Shukla | ................... B01D 15/20 530/413 |
| 2012/0283416 A1 | | 11/2012 | Frauenschuh | |
| 2014/0094593 A1 | | 4/2014 | Frauenschuh | |

FOREIGN PATENT DOCUMENTS

| | | | |
|---|---|---|---|
| EP | 0280578 A2 | 8/1988 | |
| EP | 2336172 A1 | 6/2011 | |
| JP | 2012-1462 A | 5/2012 | |
| WO | WO 2008/031020 A2 | 3/2008 | |
| WO | WO-2009058812 A1 * | 5/2009 | ............... C07K 1/18 |
| WO | WO2016031932 A1 | 3/2016 | |

OTHER PUBLICATIONS

Fahrner et al. "Industrial Purification of pharmaceutical antibodies: development, operation, and validation of chromatography processes" Biotechnology and Genetic Engineering Reviews, 18, Jul. 2001. pp. 301-327 (Year: 2001).*

Follman, D.K.; R.L. Rahrner, "Factorial screening of antibody purificatoin processes using three chromatography steps without protein A", Journal of Chromatography A, vol. 1024(1-2) (2004) 79-85.

Ghose,S.; M. Allen, B Hubbard, C. Brooks, S. Cramer, "antibody variable region interactions with Protein A: Implications for the development of generic purification process", Biotechnol Bio-eng., vol. 92 (2005) 655-673.

Levy,N.; K.N. Valente, L.H. Choe., K.H. Lee, A.M. Lenhoff, "Identification and Characterization of Host Cell Protein Product Associated Impurities in Monoclonal Antibody Processing", Biotechnol. Bioeng, vol. 111, 5 (2014) 904-912.

Nogal, B.; K. Chhiba, J.C. Emery, "Select Host cell proteins coelute with Monoclonal Antibodies in Protein A Chromatography", Biotechnol Prog vol. 28 (2012) 454-458.

Pace, A.; R. Wong, Y. T Zhang, Y-H Kao, J. Wang, "Asparagine Deamidation Dependence on Buffer Type, pH,and Temperature", J. Pharmaceutical Sciences, vol. 6, 102 (2013) 1712-1723.

Rathore, A.; R. Godavarti, V. Kumar, T. Tugcu, "Evolution of the Monoclonal Antibody Purification Platform", BioPharm Int., vol. 26, 11 (2013) 32-37.

(Continued)

*Primary Examiner* — Daniel E Kolker
*Assistant Examiner* — James L Rogers

(57) ABSTRACT

In certain embodiments, the invention provides a method of purifying a protein of interest from a mixture which comprises the protein of interest and one or more contaminants, said method comprising: a) subjecting the mixture to a first chromatography matrix, wherein the protein of interest binds to the first chromatography matrix; b) contacting the first chromatography matrix with a first wash solution which has a pH of at least 9.0, and does not comprise arginine or an arginine derivative; and c) eluting the protein of interest from the first chromatography matrix into an elution solution.

17 Claims, 6 Drawing Sheets

(56) References Cited

OTHER PUBLICATIONS

Shukla, A.; P. Hinckley, "Host Cell Protein Clearance During Protein A Chromatography: Development of an Improved Column Wash Step", Biotechnology Progress, vol. 24 (2008) 1115-1121.
Shukla, A.; B. Hubbard, T. Tressel, S. Guhan, D. Low, "Downstream Processing of Monoclonal Antibodies—Application of Platform Approaches". J Chromatography B Analyt Technol Biomed Life Sci vol. 848 (2007) 28-39.
Yumioka, R.; K. Tsumoto, T. Arakawa, D. Ejima, "Screening of effective column rinse solve for Protein A chromatography", Protein Expr Purif, vol. 70(2) (2010) 218-23.
Zhang, Q.; A. Goetze, H. Cui, J. Wylie, S. Trimble, A. Hewig, G. Flynn, "Comprehensive Tracking of Host Cell Proteins during Monoclonal Antibody Purifications Using Mass Spectrometry", mAbs, vol. 6, 3 (2014) 659-670.

* cited by examiner

USE OF ALKALINE WASHES DURING CHROMATOGRAPHY TO REMOVE IMPURITIES

CROSS REFERENCE TO RELATED APPLICATIONS

This application is a national phase application under 35 U.S.C. § 371 of International Patent Application No. PCT/US2016/021984, filed Mar. 11, 2016, which claims priority to U.S. Provisional Application 62/132,974, filed Mar. 13, 2015. each of which is hereby incorporated by reference in its entirety.

BACKGROUND OF THE INVENTION

The large-scale, economic purification of proteins is an increasingly important problem for the biopharmaceutical industry. Therapeutic proteins are typically produced using prokaryotic or eukaryotic cell lines that are engineered to express the protein of interest from a recombinant plasmid containing the gene encoding the protein. Separation of the desired protein from the mixture of components fed to the cells and cellular by-products to an adequate purity, e.g., sufficient for use as a human therapeutic, poses a formidable challenge to biologics manufacturers.

Accordingly, there is a need in the art for alternative protein purification methods that can be used to expedite the large-scale processing of protein-based therapeutics, such as antibodies from cell culture.

SUMMARY OF THE INVENTION

In certain embodiments, the present invention provides a method of purifying a protein of interest from a mixture which comprises the protein of interest and one or more contaminants, comprising: a) subjecting the mixture to a first chromatography matrix, wherein the protein of interest binds to the first chromatography matrix; b) contacting the first chromatography matrix with a first wash solution which has a pH of at least 9.0, and does not comprise arginine or an arginine derivative; and c) eluting the protein of interest from the first chromatography matrix into an elution solution. To illustrate, the contaminants are selected from host cell proteins, host cell metabolites, host cell constitutive proteins, nucleic acids, endotoxins, viruses, product related contaminants, lipids, media additives and media derivatives. Optionally, the first chromatography is an affinity chromatography (e.g., a protein A affinity chromatography or a protein G affinity chromatography). Preferably, the affinity chromatography is a protein A affinity chromatography. To illustrate, the protein of interest is selected from an antibody, an antibody fragment, and an Fc fusion protein. An exemplary protein of interest is an antibody, such as a monoclonal antibody (including, but not limited to a human, humanized and chimeric antibody).

In certain specific embodiments, the pH of the first wash solution is between about 9 and about 11. Optionally, the pH of the first wash solution is between about 9.5 and about 10.5 (e.g., 9.5, 9.6, 9.7, 9.8, 9.9, 10.0, 10.1, 10.2, 10.3, 10.4, or 10.5). An exemplary pH of the first wash solution is about 9.6. Another exemplary pH of the first wash solution is about 10.4.

In certain specific embodiments, the method further comprises, after the first wash solution, contacting the first chromatography matrix with a second wash solution which has a pH of at least 9.0, and does not comprise arginine or an arginine derivative. For example, the first wash solution comprises sodium carbonate at a concentration in a range of about 0.01-1.0 M and sodium chloride at a concentration in a range of about 0.5-2 M. For example, the second wash solution comprises sodium carbonate at a concentration in a range of about 0.01-1.0 M.

In certain specific embodiments, the mixture is subjected to one or more additional chromatography matrices. To illustrate, the first chromatography is an affinity chromatography, and the one or more additional chromatography matrices are selected from an ion exchange chromatography (e.g., an anion exchange chromatography or a cation exchange chromatography), a hydrophobic interaction chromatography, and a mix-mode chromatography. Optionally, the mixture is selected from a harvested cell culture fluid, a cell culture supernatant, and a conditioned cell culture supernatant, a cell lysate, and a clarified bulk. For example, the cell culture is a mammalian cell culture, such as a Chinese Hamster Ovary (CHO) cell culture.

DETAILED DESCRIPTION OF THE INVENTION

Figure 1:
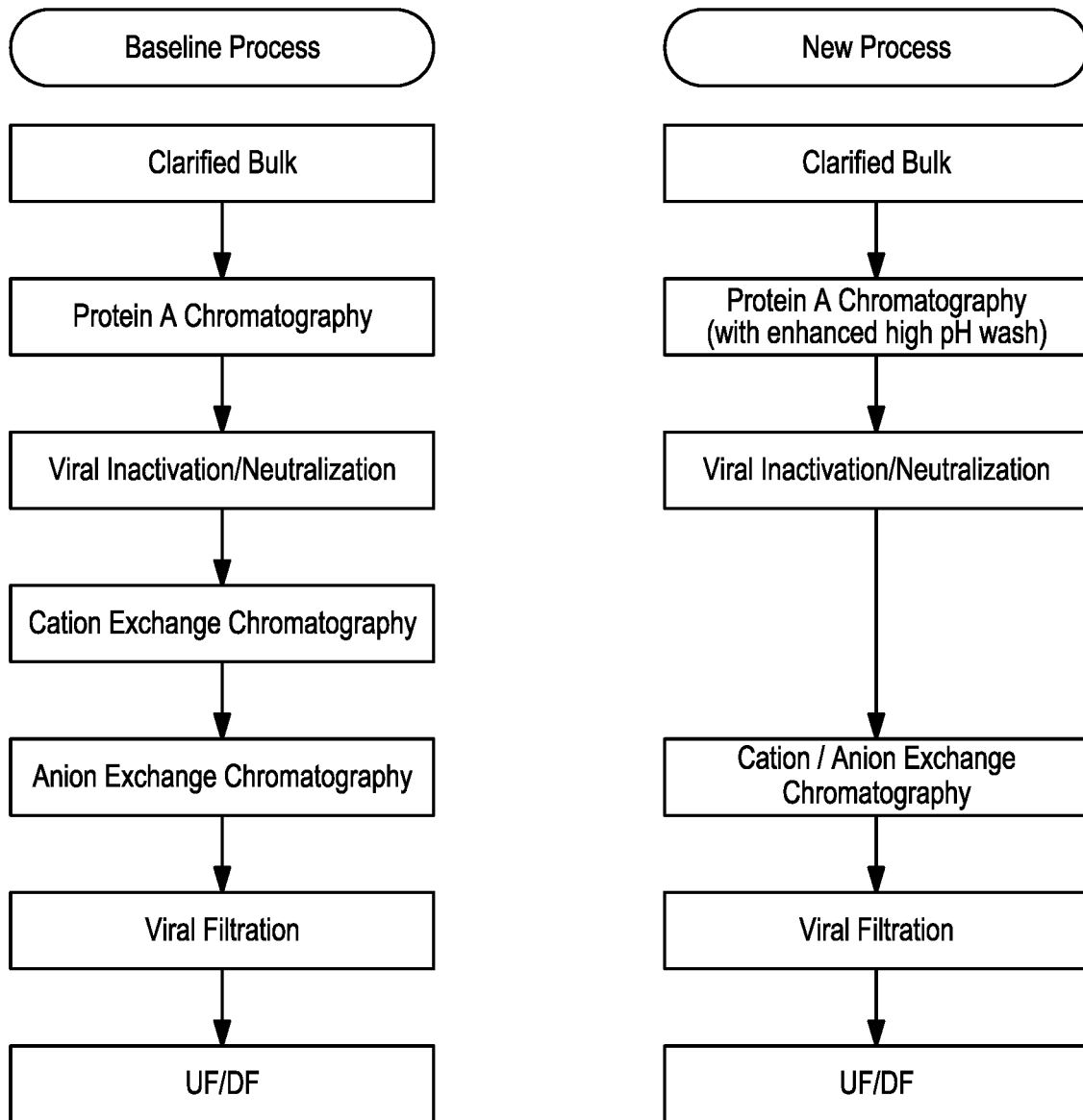
FIG. 1 shows an overview of the standard purification process and the new process.

The present invention provides a highly effective, unique approach to remove impurities during protein purification using an affinity chromatography. Specifically, the approach employs alkaline wash solutions at very high pH (e.g., 9-11). Another feature of the alkaline wash solutions is that they do not require the presence of arginine or an arginine derivative. The alkaline wash solutions are extremely effective at removing host cell protein (HCPs) from feed material applied to the affinity chromatography matrix. As shown in the working examples below, this approach is robust and can be utilized effectively for different mAb subclasses. Use of such wash solutions in affinity chromatography maintains a high process yield and the integrity of the product. In addition, the approach increases process efficiency and shortens development timelines.

In certain embodiments, the present invention provides a method of purifying a protein of interest from a mixture which comprises the protein of interest and one or more contaminants, comprising: a) subjecting the mixture to a first chromatography matrix, wherein the protein of interest binds to the first chromatography matrix; b) contacting the first chromatography matrix with a first wash solution which has a pH of at least 9.0, and does not comprise arginine or an arginine derivative; and c) eluting the protein of interest from the first chromatography matrix into an elution solution. To illustrate, the contaminants are selected from host cell proteins, host cell metabolites, host cell constitutive proteins, nucleic acids, endotoxins, viruses, product related contaminants, lipids, media additives and media derivatives.

Optionally, the first chromatography is an affinity chromatography (e.g., a protein A affinity chromatography or a protein G affinity chromatography). Preferably, the affinity chromatography is a protein A affinity chromatography. To illustrate, the protein of interest is selected from an antibody, an antibody fragment, and an Fc fusion protein. An exemplary protein of interest is an antibody, such as a monoclonal antibody (including, but not limited to a human, humanized and chimeric antibody).

In certain specific embodiments, the pH of the first wash solution is between about 9 and about 11. Optionally, the pH of the first wash solution is between about 9.5 and about 10.5 (e.g., 9.5, 9.6, 9.7, 9.8, 9.9, 10.0, 10.1, 10.2, 10.3, 10.4, or 10.5). An exemplary pH of the first wash solution is about 9.6. Another exemplary pH of the first wash solution is about 10.4.

In certain specific embodiments, the method further comprises, after the first wash solution, contacting the first chromatography matrix with a second wash solution which has a pH of at least 9.0, and does not comprise arginine or an arginine derivative. Optionally, the method further comprises, after the second wash solution, contacting the first chromatography matrix with a third wash solution which has a pH between about 6 and about 7, and does not comprise arginine or an arginine derivative. For example, the first wash solution comprises sodium carbonate at a concentration in a range of about 0.01-1.0 M and sodium chloride at a concentration in a range of about 0.5-2 M. For example, the second wash solution comprises sodium carbonate at a concentration in a range of about 0.01-1.0 M.

In certain specific embodiments, the mixture is subjected to one or more additional chromatography matrixes. To illustrate, the first chromatography is an affinity chromatography, and the one or more additional chromatography matrixes are selected from an ion exchange chromatography (e.g., an anion exchange chromatography or a cation exchange chromatography), a hydrophobic interaction chromatography, and a mix-mode chromatography. Optionally, the mixture is selected from a harvested cell culture fluid, a cell culture supernatant, and a conditioned cell culture supernatant, a cell lysate, and a clarified bulk. For example, the cell culture is a mammalian cell culture, such as a Chinese Hamster Ovary (CHO) cell culture.

I. Definitions

In order that the present disclosure may be more readily understood, certain terms are first defined. As used in this application, except as otherwise expressly provided herein, each of the following terms shall have the meaning set forth below. Additional definitions are set forth throughout the application.

As used herein, the term "protein of interest" is used in its broadest sense to include any protein (either natural or recombinant), present in a mixture, for which purification is desired. Such proteins of interest include, without limitation, hormones, growth factors, cyotokines, immunoglobulins (e.g., antibodies), and immunoglobulin-like domain-containing molecules (e.g., ankyrin or fibronectin domain-containing molecules).

As used herein, a "cell culture" refers to cells in a liquid medium. Optionally, the cell culture is contained in a bioreactor. The cells in a cell culture can be from any organism including, for example, bacteria, fungus, insects, mammals or plants. In a particular embodiment, the cells in a cell culture include cells transfected with an expression construct containing a nucleic acid that encodes a protein of interest (e.g., an antibody). Suitable liquid media include, for example, nutrient media and non-nutrient media. In a particular embodiment, the cell culture comprises a Chinese Hamster Ovary (CHO) cell line in nutrient media, not subject to purification by, for example, filtration or centrifugation.

As used herein, the term "clarified bulk" refers to a mixture from which particulate matter has been substantially removed. Clarified bulk includes cell culture, or cell lysate from which cells or cell debris has been substantially removed by, for example, filtration or centrifugation.

As used herein "bioreactor" takes its art recognized meaning and refers to a chamber designed for the controlled growth of a cell culture. The bioreactor can be of any size as long as it is useful for the culturing of cells, e.g., mammalian cells. Typically, the bioreactor will be at least 30 ml and may be at least 1, 10, 100, 250, 500, 1000, 2500, 5000, 8000, 10,000, 12,0000 liters or more, or any intermediate volume. The internal conditions of the bioreactor, including but not limited to pH and temperature, are typically controlled during the culturing period. A suitable bioreactor may be composed of (i.e., constructed of) any material that is suitable for holding cell cultures suspended in media under the culture conditions and is conductive to cell growth and viability, including glass, plastic or metal; the material(s) should not interfere with expression or stability of a protein of interest. One of ordinary skill in the art will be aware of, and will be able to choose, suitable bioreactors for use in practicing the present invention.

As used herein, a "mixture" comprises a protein of interest (for which purification is desired) and one or more contaminant, i.e., impurities. In one embodiment, the mixture is produced from a host cell or organism that expresses the protein of interest (either naturally or recombinantly). Such mixtures include, for example, cell cultures, cell lysates, and clarified bulk (e.g., clarified cell culture supernatant).

As used herein, the terms "separating" and "purifying" are used interchangeably, and refer to the selective removal of contaminants from a mixture containing a protein of interest (e.g., an antibody).

As used herein the term "contaminant" is used in its broadest sense to cover any undesired component or compound within a mixture. In cell cultures, cell lysates, or clarified bulk (e.g., clarified cell culture supernatant), contaminants include, for example, host cell nucleic acids (e.g., DNA) and host cell proteins present in a cell culture medium. Host cell contaminant proteins include, without limitation, those naturally or recombinantly produced by the host cell, as well as proteins related to or derived from the protein of interest (e.g., proteolytic fragments) and other process related contaminants. In certain embodiments, the contaminant precipitate is separated from the cell culture using an art-recognized means, such as centrifugation, sterile filtration, depth filtration and tangential flow filtration.

As used herein "centrifugation" is a process that involves the use of the centrifugal force for the sedimentation of heterogeneous mixtures with a centrifuge, used in industry and in laboratory settings. This process is used to separate two immiscible liquids. For example, in a method of the present invention, centrifugation can be used to remove a contaminant precipitation from a mixture, including without limitation, a cell culture or clarified cell culture supernatant or capture-column captured elution pool.

As used herein "sterile filtration" is a filtration method that use membrane filters, which are typically a filter with pore size 0.2 μm to effectively remove microorganisms or small particles. For example, in a method of the present invention, sterile filtration can be used to remove a contaminant precipitate from a mixture, including without limitation, a cell culture or clarified cell culture supernatant or capture-column captured elution pool.

As used herein "depth filtration" is a filtration method that uses depth filters, which are typically characterized by their design to retain particles due to a range of pore sizes within a filter matrix. The depth filter's capacity is typically defined by the depth, e.g., 10 inch or 20 inch of the matrix and thus the holding capacity for solids. For example, in a method of the present invention, depth filtration can be used to remove a contaminant precipitate from a mixture, including without limitation, a cell culture or clarified cell culture supernatant or capture-column captured elution pool.

As used herein, the term "tangential flow filtration" refers to a filtration process in which the sample mixture circulates across the top of a membrane, while applied pressure causes certain solutes and small molecules to pass through the membrane. For example, in a method of the present invention, tangential flow filtration can be used to remove a contaminant precipitate from a mixture, including without limitation, a cell culture or clarified cell culture supernatant or capture-column captured elution pool.

As used herein the term "chromatography" refers to the process by which a solute of interest, e.g., a protein of interest, in a mixture is separated from other solutes in the mixture by percolation of the mixture through an adsorbent, which adsorbs or retains a solute more or less strongly due to properties of the solute, such as pI, hydrophobicity, size and structure, under particular buffering conditions of the process. In a method of the present invention, chromatography can be used to remove contaminants after the precipitate is removed from a mixture, including without limitation, a cell culture or clarified cell culture supernatant or capture-column captured elution pool.

The terms "ion-exchange" and "ion-exchange chromatography" refer to a chromatographic process in which an ionizable solute of interest (e.g., a protein of interest in a mixture) interacts with an oppositely charged ligand linked (e.g., by covalent attachment) to a solid phase ion exchange material under appropriate conditions of pH and conductivity, such that the solute of interest interacts non-specifically with the charged compound more or less than the solute impurities or contaminants in the mixture. The contaminating solutes in the mixture can be washed from a column of the ion exchange material or are bound to or excluded from the resin, faster or slower than the solute of interest. "Ion-exchange chromatography" specifically includes cation exchange, anion exchange, and mixed mode chromatographies.

The phrase "ion exchange material" refers to a solid phase that is negatively charged (i.e., a cation exchange resin or membrane) or positively charged (i.e., an anion exchange resin or membrane). In one embodiment, the charge can be provided by attaching one or more charged ligands (or adsorbents) to the solid phase, e.g., by covalent linking. Alternatively, or in addition, the charge can be an inherent property of the solid phase (e.g., as is the case for silica, which has an overall negative charge).

A "cation exchange resin" or "cation exchange membrane" refers to a solid phase which is negatively charged, and which has free cations for exchange with cations in an aqueous solution passed over or through the solid phase. Any negatively charged ligand attached to the solid phase suitable to form the cation exchange resin can be used, e.g., a carboxylate, sulfonate and others as described below. Commercially available cation exchange resins include, but are not limited to, for example, those having a sulfonate based group (e.g., MonoS, MiniS, Source 15S and 30S, SP SEPHAROSE® Fast Flow, SP SEPHAROSE® High Performance from GE Healthcare, TOYOPEARL® SP-650S and SP-650M from Tosoh, MACRO-PREP® High S from BioRad, Ceramic HyperD S, TRISACRYL® M and LS SP and Spherodex LS SP from Pall Technologies); a sulfoethyl based group (e.g., FRACTOGEL® SE, from EMD, POROS® S-10 and S-20 from Applied Biosystems); a sulphopropyl based group (e.g., TSK Gel SP 5PW and SP-5PW-HR from Tosoh, POROS® HS-20, HS 50, and POROS® XS from Life Technologies); a sulfoisobutyl based group (e.g., FRACTOGEL® EMD $SO_3^-$ from EMD); a sulfoxyethyl based group (e.g., SE52, SE53 and Express-Ion S from Whatman), a carboxymethyl based group (e.g., CM SEPHAROSE® Fast Flow from GE Healthcare, Hydrocell CM from Biochrom Labs Inc., MACRO-PREP® CM from BioRad, Ceramic HyperD CM, TRISACRYL® M CM, TRISACRYL® LS CM, from Pall Technologies, Matrx CELLUFINE® C500 and C200 from Millipore, CM52, CM32, CM23 and Express-Ion C from Whatman, TOYOPEARL® CM-650S, CM-650M and CM-650C from Tosoh); sulfonic and carboxylic acid based groups (e.g., BAKERBOND® Carboxy-Sulfon from J. T. Baker); a carboxylic acid based group (e.g., WP CBX from J. T Baker, DOWEX® MAC-3 from Dow Liquid Separations, AMBERLITE® Weak Cation Exchangers, DOWEX® Weak Cation Exchanger, and DIAION® Weak Cation Exchangers from Sigma-Aldrich and FRACTOGEL® EMD COO— from EMD); a sulfonic acid based group (e.g., Hydrocell SP from Biochrom Labs Inc., DOWEX® Fine Mesh Strong Acid Cation Resin from Dow Liquid Separations, UNOsphere S, WP Sulfonic from J. T. Baker, SARTOBIND® S membrane from Sartorius, AMBERLITE® Strong Cation Exchangers, DOWEX® Strong Cation and DIAION® Strong Cation Exchanger from Sigma-Aldrich); and a orthophosphate based group (e.g., P11 from Whatman).

An "anion exchange resin" or "anion exchange membrane" refers to a solid phase which is positively charged, thus having one or more positively charged ligands attached thereto. Any positively charged ligand attached to the solid phase suitable to form the anionic exchange resin can be used, such as quaternary amino groups. Commercially available anion exchange resins include DEAE cellulose, POROS® PI 20, PI 50, HQ 10, HQ 20, HQ 50, D 50 from Applied Biosystems, SARTOBIND® Q from Sartorius, MonoQ, MiniQ, Source 15Q and 30Q, Q, DEAE and ANX SEPHAROSE® Fast Flow, Q SEPHAROSE® High Performance, QAE SEPHADEX® and FAST Q SEPHAROSE® (GE Healthcare), WP PEI, WP DEAM, WP QUAT from J. T. Baker, Hydrocell DEAE and Hydrocell QA from Biochrom Labs Inc., UNOsphere Q, MACRO-PREP® DEAE and MACRO-PREP® High Q from Biorad, Ceramic HyperD Q, ceramic HyperD DEAE, TRISACRYL® M and LS DEAE, Spherodex LS DEAE, QMA SPHEROSIL® LS, QMA SPHEROSIL® M and MUSTANG® Q from Pall Technologies, DOWEX® Fine Mesh Strong Base Type I and Type II Anion Resins and DOWEX® MONOSPHER E 77, weak base anion from Dow Liquid Separations, INTERCEPT® Q membrane, Matrex CELLUFINE® A200, A500, Q500, and Q800, from Millipore, FRACTOGEL® EMD TMAE, FRACTOGEL® EMD DEAE and FRACTOGEL® EMD DMAE from EMD, AMBERLITE® weak strong anion exchangers type I and II, DOWEX® weak and strong anion exchangers type I and II, DIAION® weak and strong anion exchangers type I and II, DUOLITE® from Sigma-Aldrich, TSK gel Q and DEAE 5PW and 5PW-HR, TOYOPEARL® SuperQ-650S, 650M and 650C, QAE-550C and 650S, DEAE-650M and 650C from Tosoh, QA52, DE23, DE32, DE51, DE52, DE53, Express-Ion D and Express-Ion Q from Whatman, and SARTOBIND® Q (Sartorius Corporation, New York, USA).

A "mixed mode ion exchange resin", "mixed mode ion exchange membrane" or "mixed mode" refers to a solid phase which is covalently modified with cationic, anionic, and/or hydrophobic moieties. Examples of mixed mode ion exchange resins include BAKERBOND® ABX (J. T. Baker; Phillipsburg, N.J.), ceramic hydroxyapatite type I and II and fluoride hydroxyapatite (BioRad; Hercules, Calif.) and MEP and MBI HyperCel (Pall Corporation; East Hills, N.Y.).

A "hydrophobic interaction chromatography resin" or "hydrophobic interaction chromatography membrane" refers to a solid phase which is covalently modified with phenyl, octyl, or butyl chemicals. Hydrophobic interaction chromatography is a separation technique that uses the properties of hydrophobicity to separate proteins from one another. In this type of chromatography, hydrophobic groups such as, phenyl, octyl, or butyl are attached to the stationary column. Proteins that pass through the column that have hydrophobic amino acid side chains on their surfaces are able to interact with and bind to the hydrophobic groups on the column. Examples of hydrophobic interaction chromatography resins include: (1) Butyl FF, Butyl HP, Octyl FF, Phenyl FF, Phenyl HP, Phenyl FF (high sub), Phenyl FF (low sub), Capto Phenyl ImpRes, Capto Phenyl (high sub), Capto Octyl, Capto ButylImpRes, Capto Butyl (GE Healthcare, Uppsala, Sweden); (2) TOYOPEARL® Super Butyl-550C, TOYOPEARL® Hexyl-650C, Butyl-650C, Phenyl-650C, Butyl 600 M, Phenyl-600M, PPG-600M, Butyl-650M, Phenyl-650M, Ether-650M, Butyl-650S, Phenyl-650S, Ether-650S, TSKgel Pheny-5PW, TSKgel Ether-5PW (Tosoh Bioscience, Tokyo, Japan); (3) MACRO-PREP®-butyl, MACRO-PREP®-methyl (Bio-Rad); and (4) SARTOBIND® Phenyl (Sartorius corporation, New York, USA).

II. Proteins of Interest

In certain aspects, methods of the present invention may be used to purify any protein of interest including, but not limited to, proteins having pharmaceutical, diagnostic, agricultural, and/or any of a variety of other properties that are useful in commercial, experimental or other applications. In addition, a protein of interest can be a protein therapeutic. In certain embodiments, proteins purified using methods of the present invention may be processed or modified. For example, a protein of interest in accordance with the present invention may be glycosylated.

Thus, the present invention may be used to culture cells for production of any therapeutic protein, such as pharmaceutically or commercially relevant enzymes, receptors, receptor fusion proteins, antibodies (e.g., monoclonal or polyclonal antibodies), antigen-binding fragments of an antibody, Fc fusion proteins, cytokines, hormones, regulatory factors, growth factors, coagulation/clotting factors, or antigen-binding agents. The above list of proteins is merely exemplary in nature, and is not intended to be a limiting recitation. One of ordinary skill in the art will know that other proteins can be produced in accordance with the present invention, and will be able to use methods disclosed herein to produce such proteins.

In one particular embodiment of the invention, the protein purified using the method of the invention is an antibody.

The term "antibody" is used in the broadest sense to cover monoclonal antibodies (including full length monoclonal antibodies), polyclonal antibodies, multispecific antibodies (e.g., bispecific antibodies), antibody fragments, immunoadhesins and antibody-immunoadhesin chimerias.

An "antibody fragment" includes at least a portion of a full length antibody and typically an antigen binding or variable region thereof. Examples of antibody fragments include Fab, Fab', F(ab)$_2$, and Fv fragments; single-chain antibody molecules; diabodies; linear antibodies; and multispecific antibodies formed from engineered antibody fragments.

The term "monoclonal antibody" is used in the conventional sense to refer to an antibody obtained from a population of substantially homogeneous antibodies such that the individual antibodies comprising the population are identical except for possible naturally occurring mutations that may be present in minor amounts. Monoclonal antibodies are highly specific, being directed against a single antigenic site. This is in contrast with polyclonal antibody preparations which typically include varied antibodies directed against different determinants (epitopes) of an antigen, whereas monoclonal antibodies are directed against a single determinant on the antigen. The term "monoclonal", in describing antibodies, indicates the character of the antibody as being obtained from a substantially homogeneous population of antibodies, and is not to be construed as requiring production of the antibody by any particular method. For example, monoclonal antibodies used in the present invention can be produced using conventional hybridoma technology first described by Kohler et al., *Nature*, 256:495 (1975), or they can be made using recombinant DNA methods (see, e.g., U.S. Pat. No. 4,816,567). Monoclonal antibodies can also be isolated from phage antibody libraries, e.g., using the techniques described in Clackson et al., *Nature*, 352:624-628 (1991); Marks et al., *J. Mol. Biol.*, 222:581-597 (1991); and U.S. Pat. Nos. 5,223,409; 5,403,484; 5,571,698; 5,427,908; 5,580,717; 5,969,108; 6,172,197; 5,885,793; 6,521,404; 6,544,731; 6,555,313; 6,582,915; and 6,593,081).

The monoclonal antibodies described herein include "chimeric" and "humanized" antibodies in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired biological activity (U.S. Pat. No. 4,816,567; and Morrison et al., *Proc. Natl. Acad. Sci. USA*, 81:6851-6855 (1984)). "Humanized" forms of non-human (e.g., murine) antibodies are chimeric antibodies which contain minimal sequence derived from non-human immunoglobulin. For the most part, humanized antibodies are human immunoglobulins (recipient antibody) in which the hypervariable region residues of the recipient are replaced by hypervariable region residues from a non-human species (donor antibody) such as mouse, rat, rabbit or nonhuman primate having the desired specificity, affinity, and capacity. In some instances, Fv framework region (FR) residues of the human immunoglobulin are replaced by corresponding non-human residues. Furthermore, humanized antibodies may comprise residues which are not found in the recipient antibody or in the donor antibody. These modifications are made to further refine antibody performance. In general, the humanized antibody will comprise substantially all of at least one, and typically two, variable domains, in which all or substantially all of the hypervariable loops correspond to those of a non-human immunoglobulin and all or substantially all of the FR regions are those of a human immunoglobulin sequence. The humanized antibody optionally also will comprise at least a portion of an immunoglobulin constant region (Fc), typically that of a human immunoglobulin. For further details, see Jones et al., *Nature,* 321:522-525 (1986); Riechmann et al., *Nature,* 332:323-329 (1988); and Presta, *Curr. Op. Struct. Biol.,* 2:593-596 (1992).

Chimeric or humanized antibodies can be prepared based on the sequence of a murine monoclonal antibody prepared as described above. DNA encoding the heavy and light chain immunoglobulins can be obtained from the murine hybridoma of interest and engineered to contain non-murine (e.g., human) immunoglobulin sequences using standard molecular biology techniques. For example, to create a chimeric antibody, the murine variable regions can be linked to human constant regions using methods known in the art (see e.g., U.S. Pat. No. 4,816,567 to Cabilly et al.). To create a humanized antibody, the murine CDR regions can be inserted into a human framework using methods known in the art (see, e.g., U.S. Pat. No. 5,225,539 to Winter, and U.S. Pat. Nos. 5,530,101; 5,585,089; 5,693,762; and 6,180,370 to Queen et al.).

The monoclonal antibodies described herein also include "human" antibodies, which can be isolated from various sources, including, e.g., from the blood of a human patient or recombinantly prepared using transgenic animals. Examples of such transgenic animals include KM-MOUSE® (Medarex, Inc., Princeton, N.J.) which has a human heavy chain transgene and a human light chain transchromosome (see WO 02/43478), XENOMOUSE® (Abgenix, Inc., Fremont Calif.; described in, e.g., U.S. Pat. Nos. 5,939,598; 6,075,181; 6,114,598; 6,150,584; and 6,162,963 to Kucherlapati et al.), and HUMAB-MOUSE® (Medarex, Inc.; described in, e.g., Taylor, L. et al., *Nucleic Acids Research,* 20:6287-6295 (1992); Chen, J. et al., *International Immunology,* 5:647-656 (1993); Tuaillon et al., *Proc. Natl. Acad. Sci. USA,* 90:3720-3724 (1993); Choi et al., *Nature Genetics,* 4:117-123 (1993); Chen, J. et al., *EMBO J.,* 12:821-830 (1993); Tuaillon et al., *J. Immunol.,* 152:2912-2920 (1994); Taylor, L. et al., *International Immunology,* 6:579-591 (1994); and Fishwild, D. et al., *Nature Biotechnology,* 14:845-851 (1996); U.S. Pat. Nos. 5,545,806; 5,569,825; 5,625,126; 5,633,425; 5,789,650; 5,877,397; 5,661,016; 5,814,318; 5,874,299; 5,770,429; and 5,545,807; and PCT Publication Nos. WO 92/03918, WO 93/12227, WO 94/25585, WO 97/13852, WO 98/24884, WO 99/45962, and WO 01/14424 to Korman et al.). Human monoclonal antibodies of the invention can also be prepared using SCID mice into which human immune cells have been reconstituted such that a human antibody response can be generated upon immunization. Such mice are described in, for example, U.S. Pat. Nos. 5,476,996 and 5,698,767 to Wilson et al.

III. Mixtures Containing a Protein of Interest

The methods of the invention can be applied to any mixture containing a protein of interest. In one embodiment, the mixture is obtained from or produced by living cells that express the protein to be purified (e.g., naturally or by genetic engineering). Optionally, the cells in a cell culture include cells transfected with an expression construct containing a nucleic acid that encodes a protein of interest. Methods of genetically engineering cells to produce proteins are well known in the art. See, e.g., Ausubel et al., eds., *Current Protocols in Molecular Biology,* Wiley, New York (1990) and U.S. Pat. Nos. 5,534,615 and 4,816,567, each of which are specifically incorporated herein by reference. Such methods include introducing nucleic acids that encode and allow expression of the protein into living host cells. These host cells can be bacterial cells, fungal cells, insect cells or, preferably, animal cells grown in culture. Bacterial host cells include, but are not limited to *E. coli* cells. Examples of suitable *E. coli* strains include: HB101, DH5α, GM2929, JM109, KW251, NM538, NM539, and any *E. coli* strain that fails to cleave foreign DNA. Fungal host cells that can be used include, but are not limited to, *Saccharomyces cerevisiae, Pichia pastoris* and *Aspergillus* cells. Insect cells that can be used include, but are not limited to, *Bombyx mori, Mamestra drassicae, Spodoptera frugiperda, Trichoplusia ni, Drosophilia melanogaster.*

A number of mammalian cell lines are suitable host cells for expression of proteins of interest. Mammalian host cell lines include, for example, COS, PER.C6, TM4, VERO076, DXB11, MDCK, BRL-3A, W138, Hep G2, MMT, MRC 5, FS4, CHO, 293T, A431, 3T3, CV-1, C3H10T1/2, Colo205, 293, HeLa, L cells, BHK, HL-60, FRhL-2, U937, HaK, Jurkat cells, Rat2, BaF3, 32D, FDCP-1, PC12, M1x, murine myelomas (e.g., SP2/0 and NS0) and C2C12 cells, as well as transformed primate cell lines, hybridomas, normal diploid cells, and cell strains derived from in vitro culture of primary tissue and primary explants. New animal cell lines can be established using methods well known by those skilled in the art (e.g., by transformation, viral infection, and/or selection). Any eukaryotic cell that is capable of expressing the protein of interest may be used in the disclosed cell culture methods. Numerous cell lines are available from commercial sources such as the American Type Culture Collection (ATCC®). In one embodiment of the invention, the cell culture, e.g., the large-scale cell culture, employs hybridoma cells. The construction of antibody-producing hybridoma cells is well known in the art. In one embodiment of the invention, the cell culture, e.g., the large-scale cell culture, employs CHO cells to produce the protein of interest such as an antibody (see, e.g., WO 94/11026). Various types of CHO cells are known in the art, e.g., CHO-K1, CHO-DG44, CHO-DXB11, CHO/dhfr⁻ and CHO-S.

In a specific embodiment, methods of the present invention comprise effectively removing contaminants from a mixture (e.g., a cell culture, cell lysate or clarified bulk) which contains a high concentration of a protein of interest (e.g., an antibody). For example, the concentration of a protein of interest may range from about 0.5 to about 50 mg/ml (e.g., 0.5, 1, 5, 10, 15, 20, 25, 30, 35, 40, 45 or 50 mg/ml).

Preparation of mixtures initially depends on the manner of expression of the protein. Some cell systems directly secrete the protein (e.g., an antibody) from the cell into the surrounding growth media, while other systems retain the antibody intracellularly. For proteins produced intracellularly, the cell can be disrupted using any of a variety of methods, such as mechanical shear, osmotic shock, and enzymatic treatment. The disruption releases the entire contents of the cell into the homogenate, and in addition produces subcellular fragments which can be removed by centrifugation or by filtration. A similar problem arises, although to a lesser extent, with directly secreted proteins due to the natural death of cells and release of intracellular host cell proteins during the course of the protein production run.

In one embodiment, cells or cellular debris are removed from the mixture, for example, to prepare clarified bulk. The methods of the invention can employ any suitable methodology to remove cells or cellular debris. If the protein is produced intracellularly, as a first step, the particulate debris, either host cells or lysed fragments, can be removed, for example, by a centrifugation or filtration step in order to prepare a mixture which is then subjected to purification according the methods described herein (i.e., from which a protein of interest is purified). If the protein is secreted into the medium, the recombinant host cells may be separated from the cell culture medium by, e.g., centrifugation, tangential flow filtration or depth filtration, in order to prepare a mixture from which a protein of interest is purified.

IV. High pH (Alkaline) Wash Solutions

The methods of the invention involve contacting a first chromatography matrix (e.g., affinity chromatography matrix) with an alkaline wash solution having a pH of at least 9.0. Such alkaline wash solution does not require the presence of arginine or an arginine derivative. Optionally, such alkaline wash solution may or may not comprise a non-buffering salt.

In certain embodiments, the pH of the alkaline wash solution is between about 9 and about 11. Optionally, the pH of the first wash solution is between about 9.5 and about 10.5 (e.g., 9.5, 9.6, 9.7, 9.8, 9.9, 10.0, 10.1, 10.2, 10.3, 10.4, or 10.5). An exemplary pH of the first wash solution is about 9.6. Another exemplary pH of the first wash solution is about 10.4. Optionally, the alkaline wash solution comprises sodium carbonate. Optionally, the alkaline wash solution comprises sodium chloride. In a specific embodiment, the alkaline wash solution comprises sodium carbonate at a concentration in a range of about 0.01-1.0 M and sodium chloride at a concentration in a range of about 0.5-2 M, having a pH between about 9.5 and about 10.5.

Optionally, the method further comprises contacting the first chromatography matrix (e.g., an affinity chromatography matrix) with a second alkaline wash solution. The second alkaline wash solution has a pH of at least 9.0, and does not comprise arginine or an arginine derivative. For example, the second alkaline wash solution comprises sodium carbonate at a concentration in a range of about 0.01-1.0 M.

In certain embodiments, the mixture is subjected to one or more additional chromatography matrixes, following the first chromatography purification. For example, the one or more additional chromatography matrices are selected from an ion exchange chromatography (e.g., an anion exchange chromatography or a cation exchange chromatography), a hydrophobic interaction chromatography, and a mix-mode chromatography.

The present disclosure is further illustrated by the following examples, which should not be construed as further limiting. The contents of all figures and all references, patents and published patent applications cited throughout this application are expressly incorporated herein by reference in their entireties.

Example 1

Introduction

Due to clinical demand, numerous monoclonal antibodies are currently under development for their use as therapeutics. In competition to market, biopharmaceutical companies are continuously looking to accelerate development timelines and create more efficient processes in pre-clinical and clinical manufacturing. One approach is to improve and streamline purification schemes to meet required product specifications. For this reason, maximization of impurity clearance from each unit operation is desirable [1,4]. However, purification feed streams contain various impurities that are critical to remove and can be challenging to remove, including host cell protein, DNA, adventitious and endogenous viruses, endotoxin, and aggregates. Industrial purification development closely follows these product quality attributes and has defined general guidance for product acceptance criteria (Table 1) [2,3,4]. Ideally, each unit operation in a multi-stage purification scheme should have a designated role in overall product quality, as unnecessary purification steps can often decrease protein recovery, and increase operation time and cost. Nevertheless, extensive purification schemes and orthogonal approaches are often required for impurity clearance to ensure process robustness.

Affinity separation is the most selective type of chromatography, as it separates on the basis of a reversible, highly specific interaction between a mAb and a ligand covalently coupled to a matrix [1,4,16]. Affinity chromatography using Protein A is often a key selection for downstream purification schemes, as it can provide upwards of 98% removal of impurities from monoclonal antibody feed streams [1,5]. However, processes utilizing Protein A often still require two to three subsequent chromatography polishing steps [2,3]. Further, affinity chromatography is one of the most expensive unit operations for downstream processing [15]. For these reasons, development efforts are often focused on maximizing impurity clearance for affinity capture chromatography using Protein A.

Therefore, optimization of affinity chromatography performance, driven by the improvement of impurity clearance has been of great interest. For more than two decades, the development of enhanced pre-elution washes have been applied to protein A affinity chromatography. Several lines of evidence have shown that the addition of salts, organic solvents, nonionic surfactants, chaotropes, hydrophobic modifiers, and amino acids, all have been shown to reduce HCP content and aggregate content of the eluted IgG. [1,6,7,18,19]. While promising, characterization of their overall effects on the antibody has been meager to nonexistent. In this study, Applicants test the unconventional strategy of using alkaline washes to improve impurity clearance during affinity chromatography. Applicants report the application of alkaline pre-elution washes at pH 9.6 and 10.4, and apply a panel of analytical techniques to characterize the state and quality of the eluted antibody. These analyses include SEC-UPLC, IEF, CE-SDS, SEC-MALS, Binding ELISA, Differential Scanning Calorimetry, Circular Dichroism, CHO-HCP ELISA, DNA, and residual ProA.

The "baseline" ProA capture process (FIG. 1) utilizes conditions that are generally considered an industry standard, whereby all chromatography buffers have a pH one or more units below the isoelectric point of the mAb. Binding and wash steps are performed at a neutral pH and product is eluted at an acidic pH [3,5,6]. Here the baseline capture step was made more efficient by developing a unique, "alkaline pH wash strategy" (FIG. 1). After the binding, alkaline pH washes are applied. The mAb is subsequently washed with buffer at neutral pH and eluted as in the baseline process. Implementation of the alkaline pH wash strategy made the purification scheme more efficient and the elimination of a second polishing step was enabled. One of the concerns with implementing this strategy was using alkaline pH conditions can be associated with product instability, such as deamidation, protein unfolding, and aggregate formation [3,8]. After a comparison of the baseline chromatography process to a capture process that employs high pH washes for 3 different products, the theorized product instability was not observed. Furthermore, implementation of alkaline pH washes is particularly effective at removing product related impurities. Here we describe an unconventional strategy of using alkaline pH washes to eliminate the necessity of a process step and thereby create a more efficient, cost effective process.

TABLE 1

Important Quality Attributes and Accepted Acceptance Criteria Used in This Study

| | Quality Attributes | Acceptance Criteria |
|---|---|---|
| Impurity | Residual CHO-DNA | ≤10 pg/mg |
| | Residual CHO-HCP | ≤100 ng/mg |
| | Residual Protein A | ≤100 ng/mg |
| | Residual Insulin | ≤100 ng/mg |
| Purity | SEC-HPLC (% Monomer) | ≥95% |
| | SEC-HPLC (% HMW) | ≤4% |
| | pI Charge Variant (iCIEF) | Comparable to reference standard |
| | % SDS - Non-Reduced Purity of Major Band | ≥90% |
| | % SDS-Reduced Purity of Heavy and Light Chain Bands | ≥90% |

Materials and Methods

Cell Culture

Cell culture supernatants from Chinese Hamster Ovary (CHO) cells containing fully human monoclonal antibodies were used. mAb 1 is an IgG type 4 molecule with a pI of 7.6, mAb2 is IgG 1 molecule with pI of 8.4, and mAb 3 is an IgG1 with pI of 9.2.

Chromatography

GE Healthcare's MabSelect resin was used for all capture chromatography experiments. Preparative scale column-based chromatography experiments were carried out using an ÄKTA Avant instrument (GE Lifesciences) controlled by Unicorn 6.3 software. All columns were packed in the laboratory according to the resin manufacturer's recommendations.

Baseline ProA Capture and Wash Additive Screen

Following load application, the column is washed first with PBS, pH 7.4 and second with 5 mM Succinic Acid, pH 5.8. The mAb is eluted from the column using a 10 mM phosphoric acid, pH 3.0 buffer. To assess the chromatographic performance with the addition of wash additives, an additional variable wash was inserted between wash 1 and wash 2. The variable washes tested included 20 mM Succinic Acid 500 mM NaCl, 500 mM L-Arginine pH 5.8, 20 mM Succinic Acid 0.1% Triton X-100 pH 5.8, 20 mM Succinic Acid 5% PEG 400 pH 5.8, and 17 mM Sodium Phosphate 4% Caprylic Acid pH 7.4.

ProA Capture Using High pH Wash Strategy

Following load application, the column is first washed with PBS, pH 7.4 buffer, followed by a second wash step with 200 mM sodium carbonate, 1M sodium chloride buffer, pH 9.6 or 10.4. The second wash step is followed by a third wash step using 100 mM sodium carbonate buffer, pH 9.6 or 10.4, which is followed by a fourth wash step using 35 mM sodium phosphate, pH 6.0 buffer. The mAb is eluted from the column using a 10 mM phosphoric acid, pH 3.0 buffer.

Viral Inactivation, Neutralization and Filtration

Following elution, the product pool from Affinity Chromatography was subjected to low pH viral inactivation by adjustment of product to low pH (3.4 to 3.6) using 0.1 N HCl followed by a 1 hour hold. The product was subsequently neutralized (7.0 to 7.4) using 2 M Tris. Post neutralization the product pool was filtered using 0.2 µM filter.

ELISA—CHO Host Cell Proteins Analysis

ELISA for quantification of residual CHO host cell proteins (CHO-HCP) was conducted in a high throughput manner using the TECAN® liquid handling system. Host cell proteins levels in samples were quantified using the CHO Host Cell proteins 3rd generation kit (Cat # F550, Cygnus Technologies, Southport, N.C.), according to the manufacturer's protocol. Absorbance was measured at 450/650 nm using TECAN® Infinite M1000 Pro reader.

Residual DNA Analysis

Real-time quantitative PCR (RT-PCR) was used to determine the residual CHO-DNA level in the samples. RT-PCR was carried out with the SYBR® green PCR master mix (Bio-Rad Laboratories, Hercules, Calif., USA) using the MyiQ Single-Color Real-Time PCR detection system (Bio-Rad Lab., Hercules, Calif., USA) according to the manufacturer's instructions.

Residual Protein A Analysis

ELISA for quantification of residual protein A (rProA) was conducted in a high throughput manner using the TECAN® liquid handling system. Residual protein A was quantified using the residual protein A kit (Cat #9333-1, Repligen), according to manufacturer's protocol. Absorbance was measured at 450/650 nm using TECAN® Infinite M1000 Pro reader.

Circular Dichroism

Circular dichroism spectra were collected with a Jasco J-815 CD spectrophotometer equipped with a thermostated six cell changer. mAb Samples were diluted in their corresponding buffers to 0.25 mg/mL and spectra were collected from 260 to 195 nm in 1.0 mm path length quartz cells at 25° C. Data were processed with SpectraManager software (Jasco) to normalize buffer corrected spectra to mean residue ellipticity based on the experimental peptide concentration, MW, and number of amino acids for each mAb.

Differential Scanning Calorimetry

To ascertain thermal stability profiles, DSC was performed for mAbs from each lot. Samples were normalized to 0.75 mg/mL in their corresponding process buffer. Scanning was conducted on a MICROCAL® Capillary DSC using a temperature ramp from 10-100° C. at a ramp rate of 90° C./hr. Scanning profiles of buffer alone were subtracted from sample signals and data were fit to a non-2-state model using MICROCAL® Origin 7.0 analysis software to obtain denaturation midpoint (Tm) values.

SE-UPLC

Size exclusion chromatography was used to assess mAb purity after purification by each capture strategy using Waters' Acquity H-Class Bio UPLC®. An Acquity UPLC® BEH200 SEC 1.7 µm column (4.6×150 mm) was used to perform this assay where the mobile phase consisted of PBS at pH 6.8 and was run at a flow rate of 1 mL/min. The column was maintained at 25° C. throughout the run.

SEC-MALS

The mAbs were examined by size-exclusion chromatography coupled to an inline multi-angle light scattering detector (SEC-MALS). Isocratic separations were performed on a Shodex PROTEIN KW-803 column connected to an Prominence Shimadzu UFLC in buffer containing 200 mM Potassium Phosphate 150 mM Sodium Chloride, pH 6.8, containing 0.02% Sodium Azide at a flow rate of 0.5 mL/min. Samples of 50 μg were injected onto the column using a SIL-20AC Prominence Shimadzu auto-sampler, and data were obtained from three online detectors connected in series; a Prominence SPD-20AD diode array UV/vis spectrophotometer followed by a Wyatt miniDAWN TREOS® Multi-Angle Light Scattering Detector then a Wyatt OPTI-LAB® T-REX Refractive Index Detector. Data were collected and analyzed using Astra (Wyatt) and Labsolutions (Shimadzu) software. Molecular weights and percentages of size variants were reported as obtained and summarized by the expert analyst as being comparable or not comparable.

iCIEF

Capillary isoelectric focusing with whole-column imaging (iCIEF) was performed to understand the distribution of relative abundance of mAb isoelectric point (pI) isoforms and degradants. The sample pI distribution was reported in three partitions: acidic group, main peak, and basic group compared to the pI distribution of reference standard in each experiment. The pI markers (6.14 and 9.46) are included and used to calibrate pI value in each injection. Relative abundance is calculated from each electropherogram by integrating the area under sample-derived peaks and representing the sum of peaks in each partition as a fraction of the total area integral (% Area).

CE-SDS

Capillary electrophoresis in SDS-containing gel-filled capillaries was performed to measure the molecular weight (MW) distribution of mAb-related protein species (subunits, contaminants and degradants) relative abundance. Proteins are separated based on their size and electrophoretic mobility. This method used a capillary of 30 cm (50 μm ID) total length, effective length of 20 cm and fixed point detection of 214 nm absorbance. Within-injection relative migration time is calibrated to an internal standard (10 kDa) present in every sample. The relative migration times and corrected peak areas were calculated and compared to bracketing reference standard injections. The relative abundance of the CE-SDS distributions was evaluated separately under reduced and non-reduced conditions.

Binding ELISA

Microplates were coated with antigens at 0.5-2.0 μg/mL. The plates were washed with 0.05% PBST and then blocked. The plates were subsequently washed again and the mAb was added at 12 different concentrations and incubated. After washing, HRP-conjugated secondary antibody was added. Post-incubation, plates were washed and TMB substrate was added. Signals were measured at 450 nm and 650 nm on a plate reader (Tecan Infinite M1000 Pro). Binding curves were compared to reference material to determine the percent binding capacity.

Solubility Mapping

To test solubility in each of the tested wash buffers, mAbs were buffer exchanged in a high throughput manner using desalting plates (Thermo Scientific, Cat #89808) according to the manufacturer's protocol. Following buffer exchange, the mAbs were incubated at 19-25° C. for 24 hours and solubility was assessed by SE-UPLC as described above.

Tryptic Peptide Mapping LC/MS

Antibody samples were reduced, alkylated and digested with trypsin. The tryptic peptides were separated on a C-18 column (Waters BEH C18, 1.7 u 2.1*100 mm 130 A) and detected by a UV detector at 215 nm and 280 nm, followed by a mass spectrometer (LTQ-Orbitrap-Elite). Relative quantitation was achieved by comparing peak areas of the intact peptides as well as the modified peptides in selected ion chromatograms.

Results and Discussion

In order to assess the utility of the alkaline washes at pH 9.6 and 10.4 during affinity chromatography, process and product quality attributes were examined. Impurity clearance was examined by analysis of CHO-HCP, CHO-DNA, and rProA. Purity profiles were examined using SE-HPLC, iCIEF, CE-SDS, and SEC-MALS. Functional and structural integrity of the molecule was examined using binding ELISA, CD, DSC, intact mass, N-terminal peptide mapping. The product purified with high pH washes, and baseline washes resulted in comparable recovery. For mAb 1 the recoveries were from 90% to 99%, mAb 2 are 84% to 90% and mAb 3 were 93% to 97%.

Impurity Clearance

Figure 2:
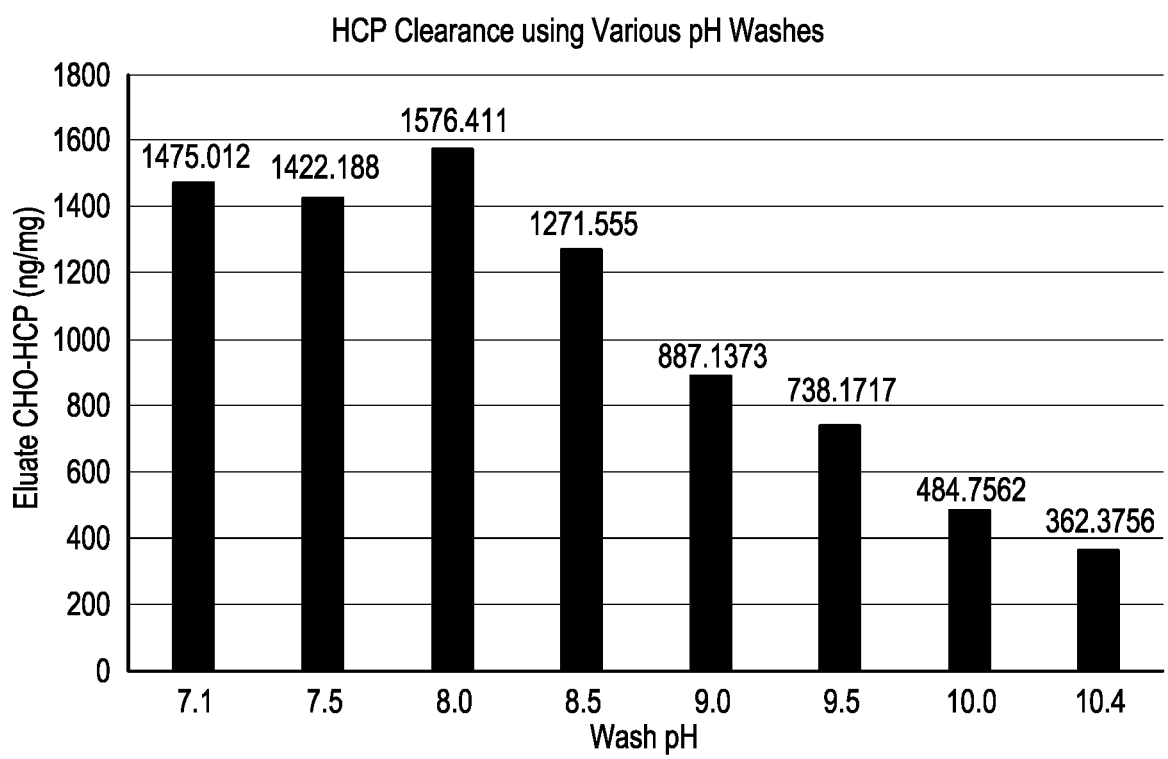
FIG. 2 shows the effect of various pH wash on reduction of CHO-HCP.

In order to maximize impurity clearance during affinity chromatography, Applicants first looked at impact of wash pH on CHO-HCP clearance. Traditionally, for Protein A chromatography following load application and chase, a pH transition wash is applied prior to elution. The transition wash is intended to bring the pH down and prepare the resin for elution. Here, Applicants added an additional wash in between ranging from pH 7.0 to 10.4 using the same conductivity as the chase to define a pH range for optimal HCP clearance. FIG. 2 illustrates that CHO-HCP levels in the eluate decrease as the wash pH increases. Based on these results the best impurity clearance was observed above pH 9.0, and the wash was particularly effective at the highest pH tested (10.4). To confirm these results and determine that this phenomenon was not specific to the monoclonal antibody, purification of 3 different mAbs was performed at wash pH 9.6 and 10.4. The study here shows that utilizing an alkaline pH wash strategy during affinity capture is effective at removing CHO host cell proteins from mAb feeds. Using an alkaline wash during affinity capture chromatography disrupts product/impurity and/or impurity/resin interactions by altering the electrostatic properties of the mAb, ProA ligand, and CHO-HCP protein surfaces while the mAb is bound on the column. During affinity chromatography, CHO-HCPs can either bind to the mAb, bind to the base matrix or bind to the proA ligand. Evidence exists that the HCP interactions with the mAb is the dominant mechanism [6,9,12]. However, it is also clear that some portion of the HCP may interact with the base matrix itself [1,2,6] or with the proA ligand [12,17]. For example, elution from affinity resin at two different pHs can result in markedly different eluate HCP levels [10,11,12]. Regardless of whether the HCP is interacting with the mAb, the base matrix, or the proA ligand, disruption of the protein-protein interactions at very high pH demonstrates to be very effective. While the product-impurity interactions are predominantly electrostatic, the binding of the Mabs to ligands are stronger. Protein A binds to antibodies mostly by induced fitting with the majority of the binding energy coming from hydrophobic interactions, with four stabilizing hydrogen bonds [20,21]. In addition, interactions such as van der Waals forces, hydrophobic interactions and electrostatic forces also contribute to the ProA-Mab binding [13]. Data here suggests that high pH washes may be used to selectively disrupt the interactions between the impurities and the mAb and/or impurities and the resin while bound to the resin.

Figure 3:
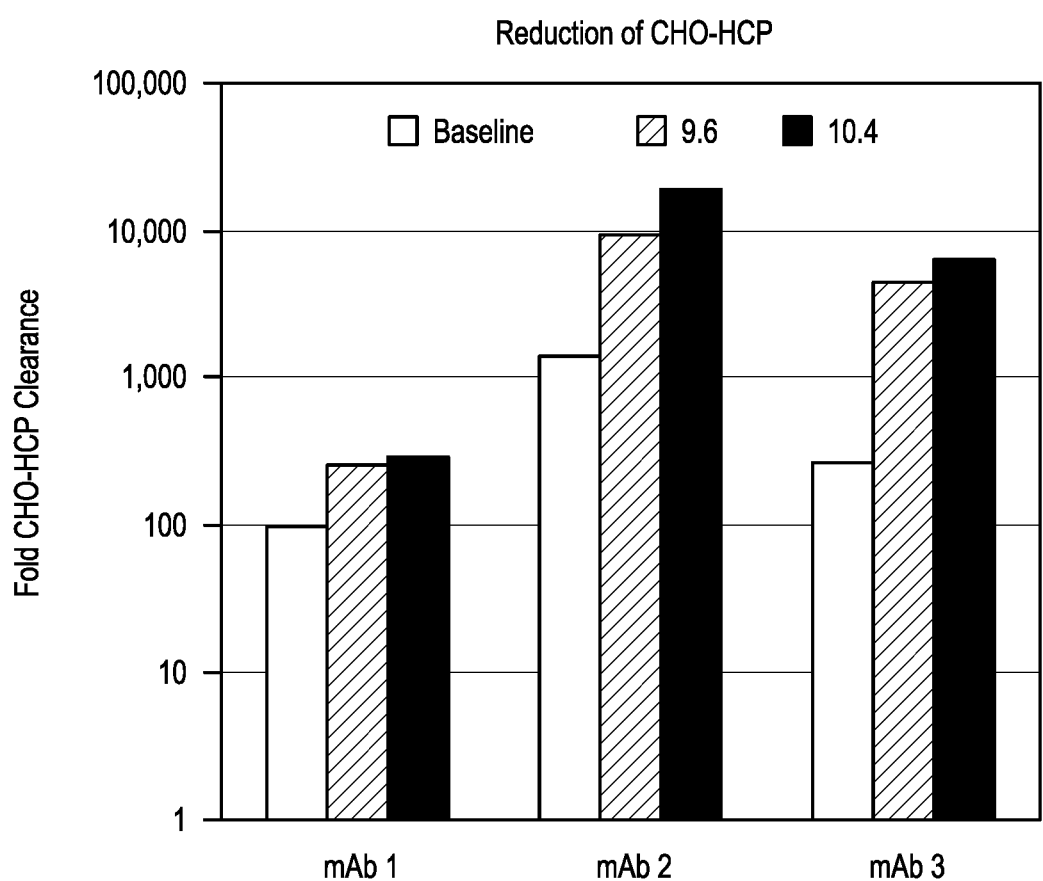
FIG. 3 shows the effect of the high pH wash on reduction of CHO-HCP.

As illustrated in FIG. 3, CHO-HCP clearance was significantly enhanced using the alkaline washes compared to the baseline conditions for all molecules. Using the alkaline wash, CHO-HCP clearance was increased ~2 to 3 fold for mAb 1, ~6 to 13 fold for mAb 2 and ~17 to 23 fold for mAb 3. An increase in CHO-HCP clearance was observed regardless of mAb subclass. Based on these results, Applicants chose to investigate alkaline washes at pH 9.6 and 10.4 for subsequent studies aimed at understanding the impact of the wash on the product quality.

Figure 4:
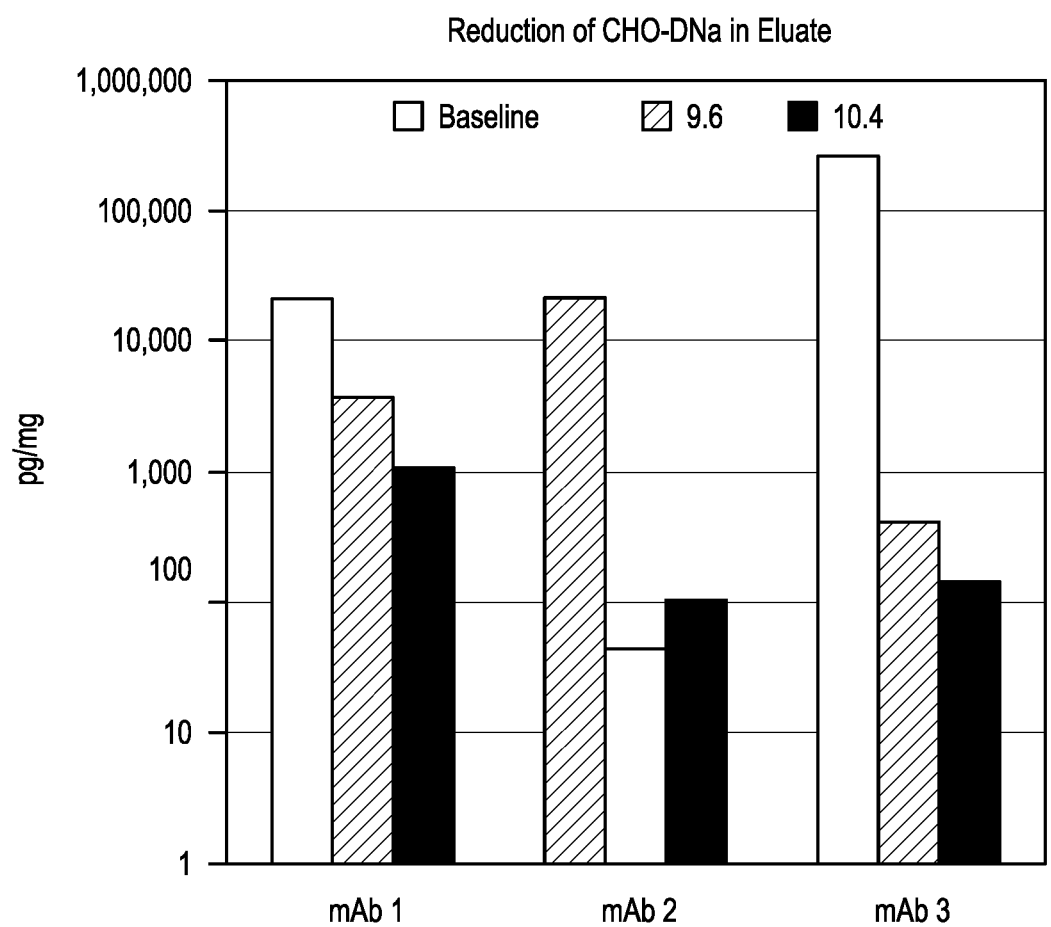
FIG. 4 shows the effect of the high pH wash on the clearance of CHO-DNA levels.

Protein A chromatography can also clear host cell DNA by 4-5 logs [2]. Not surprisingly, it was observed that there were much lower levels of DNA in the eluate when a high pH wash was utilized. As shown in FIG. 4, CHO-DNA clearance levels in the eluate were significantly decreased using the alkaline pH washes compared to the baseline conditions for all molecules. Using the alkaline pH washes CHO-DNA levels were reduced ~5 to 19 fold for mAb 1, ~209 to 490 fold for mAb 2 and ~627 to 1913 fold for mAb 3. The enhanced DNA clearance using high pH wash during affinity capture diminishes the importance of a separate DNA removal step, such as anion exchange chromatography.

Figure 5:
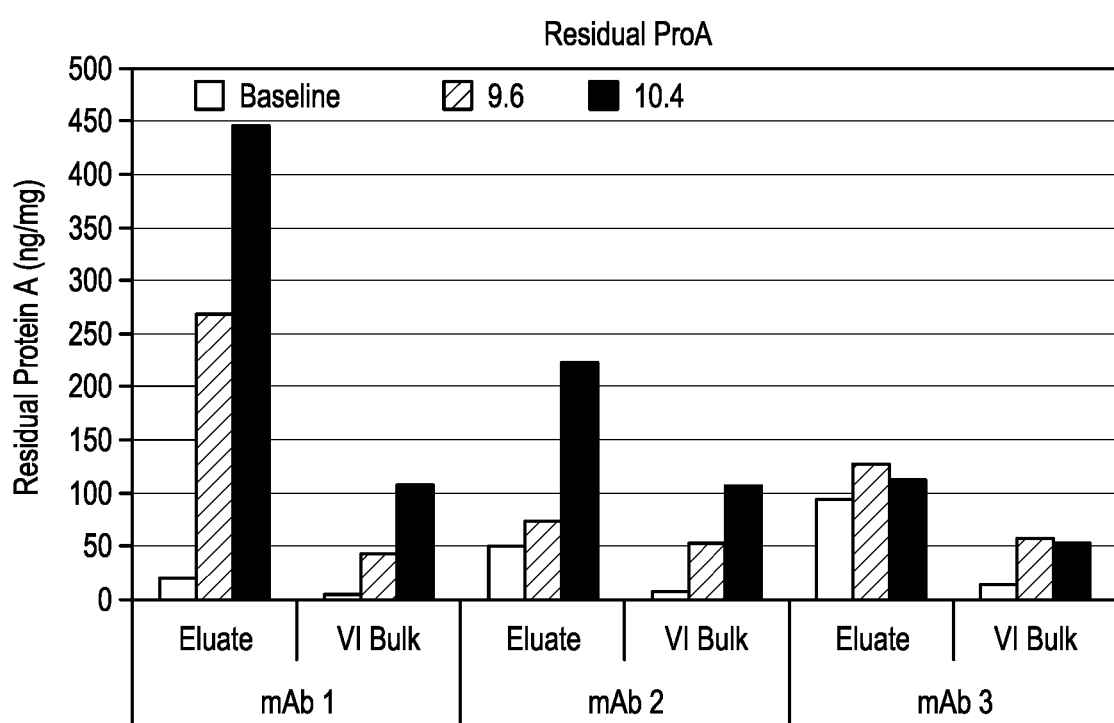
FIG. 5 shows the effect of the high pH wash on residual protein A levels.

Additionally, residual protein A was monitored to assess the impact of the alkaline pH washes on protein A chromatography. The mechanism of Protein A leaching remains to be determined. pH cycling during affinity chromatography may cause chemical breakage of the glycosidic linkages in the agarose base matrix, leading to co-elution of ProA with the mAb. This would be pronounced if free ProA is bound non-specifically and non-covalently to IgG on the resin [4]. Applicants found that the amount of ProA leached to be 25 to 450 ppm when using the high pH wash strategy. This level of ProA leaching is generally considered low and is acceptable for our process. However, the impact of the leaching on resin cycling has yet to be investigated. Further, it was observed that residual ProA is cleared during the subsequent viral inactivation step. Although the increased levels of ProA leaching are still considerably low and relatively simple to remove, there are a number of routes that can be explored to prevent the ProA leaching, the first being use of a base stable resin, such as MabSelect Sure. In addition, Applicants have observed that leaching is not as pronounced when purified product is used for feed. Therefore, it is also possible that impurities in the feed, such as proteases which are active at a higher pH, are the cause of the increased amount of ProA leaching. Indeed, several references support this concept [2]. In this case, one solution would be to add protease inhibitors in the feed. As shown in FIG. 5, higher levels of rProA leaching was observed which was effectively cleared by the subsequent viral inactivation and filtration step.

Therefore, utilizing the alkaline pH washes during affinity chromatography was able to clear impurities to acceptable levels for all molecules as shown in Table 1. This enhanced level of clearance in a single step increase process robustness and can potentially enable the elimination of subsequent polishing step to remove these impurities.

Product Purity

Purity profiles were examined using SE-UPLC, iCIEF, CE-SDS, and SEC-MALS. As illustrated in Table 2, SE-UPLC analysis demonstrates that use of the alkaline pH washes increased the product purity by over one percent for all three mAbs tested. The product quality analysis using iCIEF showed that there is no increased level of acidic or basic species due to the use of the alkaline pH wash and the pI of the molecule was unchanged. Applicants did not observe deamidation in any of the mAbs tested using the alkaline pH washes. Overall purity as measured by CE-SDS reduced and non-reduced showed no significant difference when compared to the baseline condition.

TABLE 2

Product Purity Profiles of mAbs

| Sample | SE-UPLC (% Monomer) | SE-UPLC (% HMW) | iCIEF (% Main Peak) | iCIEF (% Acidic Peak) | iCIEF (% Basic Peak) | CE-SDS (R) | CE-SDS (NR) |
|---|---|---|---|---|---|---|---|
| mAb1 Baseline | 97.1 | 2.9 | 44.3 | 21.5 | 4.3 | 100.0 | 96.0 |
| mAb 1 pH 9.6 | 99.2 | 0.9 | 43.7 | 19.4 | 4.5 | 100.0 | 98.3 |
| mAb 1 pH 10.4 | 98.8 | 1.2 | 45.0 | 23.1 | 4.8 | 100.0 | 96.0 |
| mAb 2 Baseline | 98.7 | 1.3 | 44.8 | 21.1 | 5.3 | 98.8 | 95.0 |
| mAb 2 pH 9.6 | 99.5 | 0.5 | 43.1 | 21.0 | 5.2 | 98.7 | 91.1 |
| mAb 2 pH 10.4 | 99.3 | 0.7 | 42.7 | 22.4 | 5.2 | 98.6 | 90.7 |
| mAb 3 Baseline | 95.4 | 4.6 | 39.8 | 27.1 | 4.3 | 99.2 | 97.5 |
| mAb 3 pH 9.6 | 99.6 | 0.4 | 36.2 | 30.1 | 4.2 | 99.2 | 97.5 |
| mAb 3 pH 10.4 | 99.5 | 0.5 | 35.8 | 29.3 | 3.9 | 99.1 | 97.6 |

Functional and Structural Integrity of mAbs are Maintained after Use of Extensive Alkaline pH Washes During Capture Chromatography Although mAbs are relatively stable proteins and make ideal candidates for drugs, they can be vulnerable to chemical and physical changes such as degradation and damage during the manufacturing of drug substance and drug product. Because our process strategy included alkaline pH washes studies were conducted to assess the physiochemical and structural integrity of each of the mAbs. No difference in secondary structure identity or content was detected by Circular Dichroism. Melting point, another measure of the extent of the mAbs folding, was also unaffected. In addition, activity by ELISA binding (a measure of proper folding) indicated the alkaline pH washes did not affect the folding, activity, and overall functionality of the mAbs. No difference in charge variants, oxidation or deamidation was observed for mAbs washed using a high pH by isoelectric focusing or by Tryptic Peptide Mapping LC/MS.

Multiangled Light Scattering

For each set of mAb samples, two samples were produced using the alkaline pH washes and the other two samples were produced using baseline method. As a control, the baseline samples were buffer exchanged to produce a sample in same buffer species as the two samples produced using alkaline pH wash. Results indicate that there is less than 1% aggregation in all samples. There are only slight differences in the oligomeric state of the aggregates detected. Molecular weight values for the main peak of each sample are within the error of instrumentation.

TABLE 3

SEC-MALS Analysis

| Sample Name | SE Integration by UV | | | MALS | |
|---|---|---|---|---|---|
| | % Monomer | % Dimer | % HMW (> Dimer) | MW (kDa) Peak 1 | Peak 2 |
| mAb 1 Baseline | 99.45 | 0.55 | 0.00 | 140.1 | 272.6 |
| mAb 1 pH 9.6 | 99.44 | 0.00 | 0.56 | 141.1 | 646.0 |
| mAb 1 pH 10.4 | 99.27 | 0.73 | 0.00 | 139.9 | 297.4 |
| mAb 1 (Baseline Buffer Exchanged) | 99.12 | 0.88 | 0.00 | 140.1 | 254.5 |
| mAb 2 Baseline | 99.58 | 0.00 | 0.42 | 143.6 | 3282.2 |
| mAb 2 pH 9.6 | 99.50 | 0.00 | 0.50 | 143.5 | 345.4 |
| mAb 2 pH 10.4 | 99.41 | 0.59 | 0.00 | 142.5 | 289.1 |
| mAb 2 (Baseline Buffer Exchanged) | 99.46 | 0.54 | 0.00 | 143.5 | 265.2 |
| mAb 3 Baseline | 100.00 | 0.00 | 0.00 | 141.8 | N/A |
| mAb 3 pH 9.6 | 99.71 | 0.29 | 0.00 | 141.6 | 216.9 |
| mAb 3 pH 10.4 | 99.75 | 0.25 | 0.00 | 141.6 | 296.3 |
| mAb 3 (Baseline Buffer Exchanged) | 99.90 | 0.00 | 0.10 | 143.5 | 2063.9 |

Binding ELISA

Binding ELISA examines the ability of a molecule to bind to its specific receptor and is directly related to the monoclonal antibody being folded properly. Binding ELISA data demonstrates that all mAbs, regardless of wash strategy, had similar binding to the reference standard. This demonstrates that the alkaline pH washes did not significantly impact the tertiary structure of the molecules.

TABLE 4

Binding ELISA

| Sample | mAb 1 | mAb 2 | mAb3 |
|---|---|---|---|
| | % Binding Compared to Reference Standard | | |
| Eluate Baseline | 90.0 | 100.5 | 98.0 |
| Eluate pH 9.6 | 109.3 | 99.6 | 100.2 |
| Eluate pH 10.4 | 113.1 | 87.7 | 96.1 |
| Bulk Baseline | 106.0 | 95.3 | 98.2 |
| Bulk pH 9.6 | 105.4 | 102.6 | 103.3 |
| Bulk pH 10.4 | 104.6 | 102.8 | 105.5 |
| Eluate Buffer Exchanged | 103.7 | 97.0 | 103.7 |

DSC

Differential scanning calorimetry (DSC) is a biophysical technique that can be indicative of the structural nature of the mAbs, as partially denatured mAbs will exhibit a lower melting temperature than when properly folded. DSC was measured for various mAbs purified using the alkaline pH washes as well as the baseline protocol to understand the impact of the wash on the melting point of the antibodies.

As shown in Table 5 for each set of mAb samples, the first two samples were produced using the alkaline pH washes and the last two samples were produced using baseline method. Samples 3, 7 and 11 were buffer exchanged from the baseline protocol to produce a sample in same buffer species as the two samples produced using the alkaline pH washes. The samples were buffer exchanged to control for the buffer impact on DSC.

Figure 6:
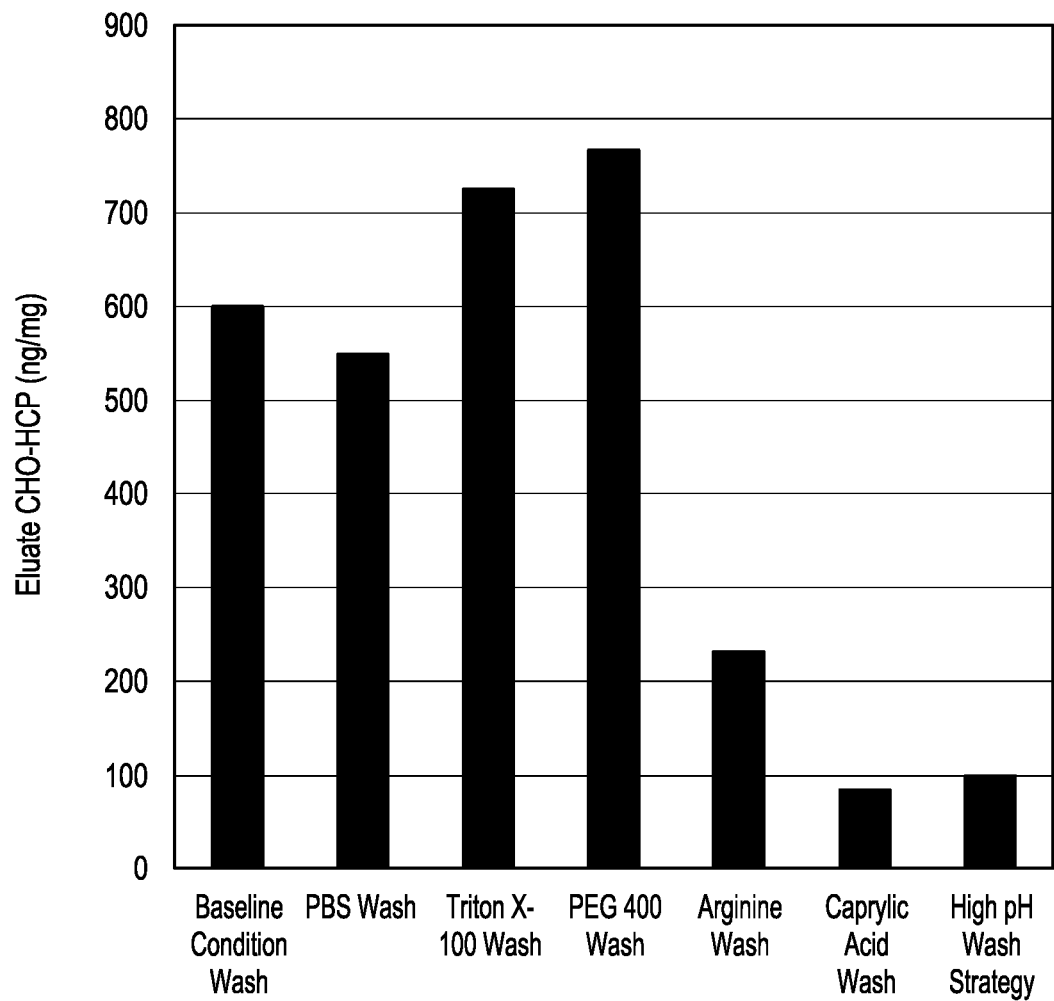
FIG. 6 shows a comparison of efficiencies of alternative processes in reducing the CHO-HCP levels.

Results indicate that the sample 4 Tm value is 1° C. below other molecules from same mAb group. As shown in FIG. 6, Tonset also appears to be shifted lower indicating possible sensitivity to the buffer or process. Since the buffer exchanged sample (sample 3) Tm value is similar to the alkaline pH wash samples (sample 1 and 2) it can be deduced that the change in Tm for this sample is due to sample buffer composition impact on DSC. Therefore, for mAb 1 there is no significant impact of the alkaline pH washes on Tm. For mAb 2, no significant differences were observed in Tm1 or Tm2 values indicating that the different wash conditons do not impact the melting point of this sample. Similar to mAb 1, mAb 3 had modestly lower Tm for sample 12 than other conditions, possibly indicating slightly less stability in this buffer condition or process. The Tm value for buffer exchanged sample (sample 11) is similar to the alkaline pH wash samples (sample 9 and 10) and therefore the change in Tm for this sample is due to sample buffer composition impact on DSC. Therefore, for mAb 3 there is no significant impact of alkaline pH washes on Tm.

TABLE 5

Differential Scanning Calorimetry

| Sample ID | Sample Name | Tm1, ° C. | Tm2, ° C. |
|---|---|---|---|
| 1 | mAb 1 pH 9.6 | 65.3 | — |
| 2 | mAb 1 pH 10.4 | 65.4 | — |
| 3 | mAb 1 (Baseline Buffer Exchanged) | 65.2 | — |
| 4 | mAb 1 Baseline | 64.2 | — |
| 5 | mAb 2 pH 9.6 | 67.3 | 82.8 |
| 6 | mAb 2 pH 10.4 | 67.2 | 82.8 |
| 7 | mAb 2 (Baseline Buffer Exchanged) | 67.2 | 82.7 |
| 8 | mAb 2 Baseline | 67.3 | 82.8 |
| 9 | mAb 3 pH 9.6 | 65.6 | 80.8 |
| 10 | mAb 3 pH 10.4 | 65.7 | 80.8 |
| 11 | mAb 3 (Baseline Buffer Exchanged) | 65.8 | 80.7 |
| 12 | mAb 3 Baseline | 65.1 | 80.6 |

Circular Dichroism

Far-UV circular dichroism (CD) spectroscopy was used to characterize the secondary structure of the three mAbs purified using both approaches. The CD spectra reference standard and mAbs under various conditions were evaluated between wavelength of 260 nm and 195 nm. The CD signal was converted from millidegree to mean residue ellipticity using the calculated molecular weight and number of amino acid residues based on amino acid sequence of each respective mAb. The far UV CD spectrum demonstrated minima at 217 and 229 nm for mAb 1, 217-218 nm for mAb 2, and 217-218 nm for mAb3. The average mean residue ellipticity for mAb1 was −3128±358 deg cm2dmol-1residue-1 (average±standard deviation for the 4 conditions) at 217 nm and −1738±204 deg cm2dmol-1residue-1 at 229 nm. The average mean residue ellipticity for mAb2 was −3477±454 deg cm2dmol-1residue-1 at 217 nm. The average mean residue ellipticity for mAb3 was −3392±83 deg cm2dmol-1residue-1 at 217 nm. Minima and spectra shape were maintained for each mAb, regardless of the protocol used to purify the mAb. Qualitative similarity in terms of the shape and the intensity of the CD spectra demonstrate that the alkaline pH wash strategy does not affect the secondary structure of the mAbs under investigation. Although there were differences between mAbs, for each individual mAb the CD spectra were qualitatively similar under all wash conditions tested. Spectra of all samples were consistent with β-sheet content.

Tryptic Peptide Mapping LC/MS

Drug substance from three processes were reduced, alkylated and digested with trypsin. The tryptic peptides were separated on a C-18 column and detected by a UV detector at 215 and 280 nms, followed by a mass spectrometer (LTQ-Orbitrap-Elite). Relative quantitation was achieved by comparing peak areas of the intact peptides as well as the modified peptides in selected ion chromatograms. Oxidation was monitored by peak area percentage of the oxidation product from an indicator peptide in the heavy chain and deamidation was monitored by peak area percentages of four deamidation products from another indicator peptide in the heavy chain. The levels of oxidation and deamidation are comparable in the baseline samples and the alkaline pH samples in all three mAbs.

TABLE 6

Tryptic Peptide Mapping LC/MS

| Sample | Oxidation % | Deamidation Product 1 % | Deamidation Product 2 % | Deamidation Product 3 % | Deamidation Product 4 % | Deamidation Product Total % |
|---|---|---|---|---|---|---|
| mAb Baseline | 3.0 | 3.3 | 4.1 | 2.0 | 3.6 | 13.0 |
| mAb 1 pH 9.6 | 2.1 | 3.8 | 4.4 | 2.0 | 3.8 | 13.9 |
| mAb 1 pH 10.4 | 1.7 | 3.9 | 4.9 | 2.0 | 4.0 | 14.8 |
| mAb 2 Baseline | 2.5 | 3.1 | 3.5 | 1.9 | 4.3 | 12.8 |
| mAb 2 pH 9.6 | 3.2 | 3.1 | 4.0 | 1.9 | 4.3 | 13.2 |
| mAb 2 pH 10.4 | 2.6 | 3.8 | 4.9 | 1.8 | 4.2 | 14.6 |
| mAb 3 Baseline | 3.9 | 2.1 | 6.0 | 2.8 | 5.5 | 16.4 |
| mAb 3 pH 9.6 | 3.3 | 3.8 | 4.7 | 2.1 | 4.5 | 15.1 |
| mAb 3 pH 10.4 | 3.4 | 2.3 | 6.6 | 2.6 | 5.3 | 16.8 |

The strategy of using alkaline washes at pH 9.6 to 10.4 is possible in part because ligand-receptor binding is a strong interaction that holds the mAb in its proper conformation and may protect it from denaturation and other damage. The range of measured affinity constants for antibody/antigen binding extends from below 105 M-1 to above 1012 M-1 [13] and for protein A ligand and the Fcγ is 107-108 at neutral pH and room temperature [14]. The binding of a ligand to a receptor puts the structure of the mAb in a lower energetic state than the structure of the mAb when it is unbound. Therefore, when bound, the mAb is further from the transition state of denaturation and is protected. Although the mAbs are in a more stable state when bound to the ligand, Applicants also looked at the potential of aggregation of the mAbs when exposed to the alkaline pH buffers when no ligand is present (Table 7). After a 24 hour incubation at room temperature, there was no change in monomeric content, indicating that the unbound mAbs are stable in these conditions.

TABLE 7

Buffer Solubility for mAbs

| Buffer Conditions | pH | mAb 1 (% Monomer) | | | mAb 2 (% Monomer) | | | mAb 3 (% Monomer) | | |
|---|---|---|---|---|---|---|---|---|---|---|
| | | Rep 1 | Rep 2 | Rep 3 | Rep 1 | Rep 2 | Rep 3 | Rep 1 | Rep 2 | Rep 3 |
| 200 mM sodium carbonate, 1M sodium chloride | 9.6 | 99.6 | 98.4 | 98.5 | 94.9 | 99.2 | 99.2 | 99.8 | 98.6 | 98.6 |
| | 10.0 | 98.5 | 98.3 | 98.4 | 99.3 | 99.3 | 99.3 | 98.6 | 98.6 | 98.6 |
| | 10.4 | 98.4 | 98.4 | 98.4 | 99.3 | 99.3 | 99.3 | 98.7 | 98.6 | 98.6 |
| 100 mM sodium carbonate | 9.6 | 99.4 | 99.4 | 99.4 | 98.7 | 98.6 | 98.4 | 98.6 | 98.6 | 98.6 |
| | 10.0 | 99.3 | 99.4 | 99.4 | 99.0 | 98.4 | 98.5 | 98.6 | 98.6 | 98.6 |
| | 10.4 | 99.3 | 99.3 | 99.3 | 98.4 | 98.4 | 98.3 | 98.6 | 98.7 | 98.6 |
| 1 X PBS | 7.4 | 99.4 | 99.6 | 99.5 | 100.5 | 100.5 | 100.5 | 98.7 | 98.6 | 98.7 |

Alternative strategies to enhance impurity clearance include use of additives in the wash during capture, such as salts, organic solvents, nonionic surfactants, chaotropes, hydrophobic modifiers, and amino acids [6,7]. FIG. 6 shows that the alkaline pH wash strategy is one of the most effective ways to reduce CHO-HCP using the wash step. In addition, the alkaline pH wash strategy does not utilize additives that could require subsequent clearance and monitoring. There is also potential for including additives in the alkaline pH wash buffers to further enhance impurity clearance.

Shukla et. al. has shown that the addition of arginine in the wash during capture is an effective way to reduce impurities in the eluate [6]. Studies were performed to compare impurity removal when utilizing the alkaline pH wash with and without arginine (Table 8). Results indicate no additional clearance was achieved with the addition of arginine in the alkaline wash.

TABLE 8

Comparison of Product and Process Quality for mAb Purified Using both Alkaline pH Strategy and Arginine Wash Strategy

| | SE-UPLC Eluate | | | | | |
|---|---|---|---|---|---|---|
| Strategy | % Recovery | % HMW | % LMW | % Monomer | CHO-HCP (ng/mg) | rProA (ng/mg) |
| Load | N/A | N/A | N/A | N/A | 716255 | N/A |
| Buffer + 0.5M L-Arginine pH 9.6 | 80 | 2.5 | BDL | 97.5 | 1160 | 125 |
| Buffer pH 9.6 | 82 | 2.6 | BDL | 97.4 | 1274 | 122 |

Implementation of an Alkaline pH Wash Strategy can Eliminate the Need for Additional Polishing Steps in mAb Purification Schemes The majority of purification processes utilize 2-3 polishing chromatography steps to meet industrial quality standards. While orthogonal methods of impurity clearance can increase process robustness, manufacturing economics drives process development to create streamlined processes. Here, Applicants demonstrate that during affinity chromatography, wash steps can be made increasingly effective, which can enable the elimination of one or more polishing steps. Table 9 illustrates that the use of the high pH wash during capture chromatography improves impurity clearance to the degree that the CEX polishing step is not needed. By exploiting the extensive nature of binding during affinity chromatography, Applicants show that aggressive pH washes can be used to enhance impurity clearance.

TABLE 9

2-Step vs. 3-Step Purification

| | 2 Step Process High Wash Capture Strategy | | | 3 Step Process Baseline Capture Strategy | | | |
|---|---|---|---|---|---|---|---|
| | Protein A | | | Protein A | | | |
| Assays | Eluate | Bulk | AEX | Eluate | Bulk | CEX | AEX |
| CHO-HCP (ng/mg) | ≤44 | 15 | BDL | 679 | 30 | 8 | 11 |
| CHO-DNA(pg/mg) | BDL | BDL | BDL | BDL | BDL | BDL | ND |
| rProA (ng/mg) | ≤48 | ≤28 | 6 | 4 | 3 | 2 | 2 |
| % Monomer (SE-HPLC) | 99.4 | 99.2 | 99.2 | 99.5 | 99.6 | 99.3 | 99.6 |

REFERENCES

[1] F. Hui Liu, M. Junfen, C. Winter, R. Bayer, Recovery and purification process development for monoclonal antibody production, mAbs 2:5, September/October (2010) 480-499
[2] P. Gagnon, Purification tools for monoclonal antibodies. Validated Biosystems Inc., Tucson, Ariz. (1996) 155-198
[3] L. Hagel, G. Jagschies, G Sofer, Handbook of Process Chromatography, 2nd Ed., Academic Press, London, (2008)
[4] U. Gottschalk, Process Scale Purification of Antibodies, John Wiley and Sons, Hoboken, N.J. (2009)
[5] A. Rathore, R. Godavarti, V. Kumar, T. Tugcu, Evolution of the Monoclonal Antibody Purification Platform, BioPharm Int., 26, 11 (2013) 32-37
[6] A. Shukla, P. Hinckley, Host Cell Protein Clearance During Protein A Chromatography: Development of an Improved Column Wash Step, Biotechnology Progress, 24 (2008) 1115-1121
[7] T. Breece, R. Fahrner, J. R. Gorrell, K. P. Lazzareschi, P. Lester, D. Peng, Protein Purification. U.S. Pat. No. 6,870, 034 B2 (2005)
[8] A. Pace, R. Wong, Y. T Zhang, Y-H Kao, J. Wang, Asparagine Deamidation Dependence on Buffer Type, pH, and Temperature, J. Pharmaceutical Sciences, 6, 102 (2013) 1712-1723
[9] Q. Zhang, A. Goetze, H. Cui, J. Wylie, S. Trimble, A. Hewig, G. Flynn, Comprehensive Tracking of Host Cell Proteins during Monoclonal Antibody Purifications Using Mass Spectrometry, mAbs, 6, 3 (2014) 659-670
[10] A. Shukla, B. Hubbard, T. Tressel, S. Guhan, D. Low, Downstream Processing of Monoclonal Antibodies-Application of Platform Approaches. J Chromatography B Analyt Technol Biomed Life Sci 848 (2007) 28-39
[11] N. Levy, K. N. Valente, L. H. Choe., K. H. Lee, A. M. Lenhoff, Identification and Characterization of Host Cell Protein Product Associated Impurities in Monoclonal Antibody Processing, Biotechnol. Bioeng, 111, 5 (2014) 904-912

[12] B. Nogal, K. Chhiba, J. C. Emery, Select Host cell proteins coelute with Monoclonal Antibodies in Protein A Chromatography, Biotechnol Prog 28 (2012) 454-458

[13] E. Harlow, D. Lane, Antibodies—A laboratory manual. Cold Spring Harbor Laboratory (1988) 26

[14] P. W. Roben, A. N. Salem, G. J Silverman, Vh3 family antibodies bind domain D of staphylococcal protein A. J. Immunology, 154 (1995) 6437-6445

[15] D. K. Follman, R. L. Rahrner, Factorial screening of antibody purification processes using three chromatography steps without protein A, Journal of Chromatography A 1024(1-2) (2004) 79-85

[16] S. Ghose, M. Allen, B Hubbard, C. Brooks, S. Cramer, antibody variable region interactions with Protein A: Implications for the development of generic purification process, Biotechnol Bio-eng. 92 (2005) 655-673

[17] I. Bjorck, B. Akerstom, in; M. Boyle (Ed.), Bacterial Immunoglobulin-Binding Proteins, Vol. I, Academic Press, San Diego, p. 113

[18] S. Sun, Arginine wash in protein purification using affinity chromatography, U.S. Pat. No. 8,350,013 B2 (January 2013)

[19] R. Yumioka, K. Tsumoto, T. Arakawa, D. Ejima, Screening of effective column rinse solve for Protein A chromatography, Protein Expr Purif, 70(2) (2010) 218-23

[20] J. Deisenhofer, Crystallographic refinement and atomic models of a human Fc fragment and its complex with fragment of Bof Protein A from *Staphylococcus aureus* at 2.9 and 2.8 A resolution, Biochemistry 20 (1981) 2361-2370

[21] J. Desienhofer, T. Jones, R. Huber, J. Sjodahl, J. Sjoquist, Crystallization, crystal structure analysis and atomic model of the complex formed by human Fc fragment and fragment B of Protein A from *Staphylococcus aureus*, Hoppe-Seylars Z. Physiol. Chem. 359 (1978) 975-985

EQUIVALENTS

Those skilled in the art will recognize or be able to ascertain using no more than routine experimentation, many equivalents of the specific embodiments of the invention described herein. Such equivalents are intended to be encompassed by the following claims.

INCORPORATION BY REFERENCE

All patents, pending patent applications, and other publications cited herein are hereby incorporated by reference in their entireties.

We claim:

1. A method of purifying a protein of interest from a mixture which comprises the protein of interest and one or more contaminants, comprising:
   a) subjecting the mixture to a first chromatography matrix, wherein the protein of interest binds to the first chromatography matrix, and wherein the first chromatography is an affinity chromatography selected from a protein A affinity chromatography and a protein G affinity chromatography;
   b) contacting the first chromatography matrix with a first wash solution which has a pH of at least 9.5, and does not comprise arginine or an arginine derivative;
   c) eluting the protein of interest from the first chromatography matrix into an elution solution; and
   d) contacting the first chromatography matrix with a second wash solution which has a pH of at least 9.0, and does not comprise arginine or an arginine derivative.

2. The method of claim 1, wherein the contaminants are selected from host cell proteins, host cell metabolites, host cell constitutive proteins, nucleic acids, endotoxins, viruses, product related contaminants, lipids, media additives and media derivatives.

3. The method of claim 1, wherein the affinity chromatography is a protein A affinity chromatography.

4. The method of claim 1, wherein the protein of interest is selected from an antibody, an antibody fragment, and an Fc fusion protein.

5. The method of claim 4, wherein the antibody is a monoclonal antibody.

6. The method of claim 5, wherein the monoclonal antibody is selected from the group consisting of a human, humanized and chimeric antibody.

7. The method of claim 1, wherein the pH of the first wash solution is between about 9.5 and about 10.5.

8. The method of claim 1, wherein the pH of the first wash solution is about 9.6.

9. The method of claim 1, wherein the pH of the first wash solution is about 10.4.

10. The method of claim 1, further comprising contacting the first chromatography matrix with a third wash solution which has a pH between about 6 and about 7, and does not comprise arginine or an arginine derivative.

11. The method of claim 1, wherein the first wash solution comprises sodium carbonate at a concentration in a range of about 0.01-1.0 M and sodium chloride at a concentration in a range of about 0.5-2 M.

12. The method of claim 1, wherein the second wash solution comprises sodium carbonate at a concentration in a range of about 0.01-1.0 M.

13. The method of claim 1, wherein the mixture is subjected to one or more additional chromatography matrixes.

14. The method of claim 13, wherein the one or more additional chromatography matrices are selected from an ion exchange chromatography, a hydrophobic interaction chromatography, and a mix-mode chromatography.

15. The method of claim 1, wherein the mixture is selected from a harvested cell culture fluid, a cell culture supernatant, and a conditioned cell culture supernatant, a cell lysate, and a clarified bulk.

16. The method of claim 15, wherein the cell culture is a mammalian cell culture.

17. The method of claim 14, wherein the ion exchange chromatography is an anion exchange chromatography or a cation exchange chromatography.

* * * * *